(12) United States Patent
Suekane

(10) Patent No.: US 6,659,991 B2
(45) Date of Patent: Dec. 9, 2003

(54) ABSORPTIVE ARTICLE HAVING WING MEMBERS, AND PROCESS FOR MANUFACTURING THE SAME

(75) Inventor: Makoto Suekane, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/114,024

(22) Filed: Mar. 29, 2002

(65) Prior Publication Data

US 2002/0156445 A1 Oct. 24, 2002

Related U.S. Application Data

(63) Continuation of application No. 09/643,438, filed on Aug. 22, 2000, now Pat. No. 6,511,464.

(30) Foreign Application Priority Data

Aug. 27, 1999 (JP) .......................................... 11-241279

(51) Int. Cl.⁷ .............................................. A61F 13/15
(52) U.S. Cl. ........................... 604/385.04; 604/385.03; 604/385.01
(58) Field of Search ...................... 604/385.03, 385.04, 604/386, 387

(56) References Cited

U.S. PATENT DOCUMENTS

| | | | | |
|---|---|---|---|---|
| 4,285,343 A | * | 8/1981 | McNair ...................... 604/387 |
| 4,321,924 A | * | 3/1982 | Ahr ............................. 604/378 |
| 5,275,591 A | * | 1/1994 | Mavinkurve ................ 604/387 |
| 5,308,346 A | | 5/1994 | Sneller et al. ........... 604/385.2 |
| 5,591,147 A | * | 1/1997 | Couture-Dorschner et al. .......... 604/369 |
| 5,704,928 A | * | 1/1998 | Morita et al. ........... 604/385.23 |
| 5,921,948 A | * | 7/1999 | Kawaguchi et al. .......... 602/52 |
| 6,093,178 A | * | 7/2000 | Osborn et al. ............... 604/387 |
| 6,293,932 B1 | * | 9/2001 | Balzar et al. .......... 604/385.02 |
| 6,315,766 B1 | * | 11/2001 | Drevik ........................ 604/387 |

FOREIGN PATENT DOCUMENTS

| | | |
|---|---|---|
| DE | 4226739 A1 | 2/1994 |
| EP | 0534488 A1 | 3/1993 |
| EP | 2303291 A | 2/1997 |
| FR | 2700687 | 1/1993 |
| JP | 07118431 A * | 5/1995 |
| JP | 9-511929 | 12/1997 |
| WO | WO95/20932 | 8/1995 |
| WO | WO95/28137 | 10/1995 |
| WO | WO96/10977 | 4/1996 |

OTHER PUBLICATIONS

European Search Report dated Jul. 6, 2001.

* cited by examiner

*Primary Examiner*—Weilun Lo
*Assistant Examiner*—Jacqueline F Stephens
(74) *Attorney, Agent, or Firm*—Darby & Darby

(57) ABSTRACT

There is disclosed an absorptive article including: a body including a liquid-permeable top sheet, a back sheet and an absorbent layer sandwiched between the top sheet and the back sheet; and wing members disposed on two side portions of the body and extending outwards in the widthwise direction from the body. The wing members are jointed to the two side portions of the body while being sandwiched between the top sheet and the back sheet.

13 Claims, 9 Drawing Sheets

ABSORPTIVE ARTICLE HAVING WING MEMBERS, AND PROCESS FOR MANUFACTURING THE SAME

This is a continuation of application Ser. No. 09/643,438, filed Aug. 22, 2000 now U.S. Pat. No. 6,511,464 issued to Suckane applications is hereby incorporated herein by reference, in its entirety.

BACKGROUND OF THE INVENTION

1. Field of the Invention

The present invention relates to an absorptive article such as a sanitary napkin, a pantie liner or a urine pad. More particularly, the invention relates to an absorptive article having wings to be folded back, when worn, to the lower side of the crotch portion of an underwear, and to a process for manufacturing the absorptive article.

2. Related Art

In recent years, various types of absorptive articles such as sanitary napkins, pantie liners or urine pads have been used for absorbing the discharges such as menses or urine. Most of these absorptive articles are provided with wings on the two longitudinally extending side portions. When the absorptive article is worn, the wings are folded back to the lower side of the crotch portion of the underwear to prevent the underwear edge portions from being blotted with the discharges. In general, these wings are provided with adhesion means for attaching them to the underwear. The absorptive article can be stably worn with little dislocation if its wings are attached and adhered to the lower side of the crotch portion of the underwear.

These wings are generally formed by protruding the members constructing the body of the absorptive article integrally, that is, the joint assembly of a back sheet and a top sheet sideways of the body of the absorptive article.

Where the joint assembly of the back sheet and the top sheet is used to form the wings, however, the absorptive article has to be manufactured such that: a laminate is formed by sandwiching an absorbent layer between a back sheet material and a top sheet material; and this laminate is trimmed out to form an elliptical or hour-glass body portion and wings. Therefore, the width sizes of the back sheet material and the top sheet material for use have to be made large to form the wings by cutting. Moreover, the unnecessary, waste portions to be cut out while leaving the body portion and the wingsshare excessively wide areas in the top sheet material and the back sheet material.

In some absorptive articles of the prior art, on the other hand, the wing members are formed separately from the members forming the body so that they may be given a function different from that of the top sheet. In Japanese Unexamined Patent Publication (Kokai) No. Heisei 6-47072, for example, there is disclosed a sanitary napkin in which the wing members and the side barriers (or the sideway leakage preventing cuffs) are made of a common member. This napkin can be manufactured by reducing one step of its manufacturing process because the members to be ordinarily attached separately of each other are made of the common member.

In Japanese Unexamined Patent Publication (Kouhyou) No. Heisei 9-511929, on the other hand, there is disclosed an absorptive article in which the wing members are easily folded downward along the edge portions of the crotch portion of an underwear. These wing members are provided with zones of different extensibilities to lower the stress which will arise at the folding time.

However, the structure, in which the wing members are made of a member different from that constructing the body, has a defect that the wing members easily come out from the body. In the aforementioned example, moreover, the wing members are jointed to the surface of the top sheet or back sheet of the absorptive article so that there is a limit to the enhancement of the joint strength between the wing members and the body. Since the wing members are wholly exposed to the surface of the absorptive article, moreover, their end portions are highly probably caught, when the absorptive article is worn, to leave the body.

On the other hand, the wing members are demanded to have functions such as an easy foldability along the edge portions of the underwear or an air-permeability. If the wing members and the side barriers are made of the common member as in the former example, for example, the wing members are hard to fold downward along the edge portions of the crotch portion of the underwear. Moreover, the side barriers are ordinarily made of an impermeable material, and the wing members have an air-permeability lowered to make the inside of the underwear stuffy if they are made of the same material. In the latter case, on the contrary, the wing members having the differently extensible zones could be made of an air-permeable material and are easily folded downward along the edge portions of the crotch portion of the underwear. In the presence of the differently extensible zones, however, the foldable areas of the wing members are so widened that the wing members are hard to fold on the predetermined lines in the manufacture process. As a result, it is difficult to raise the production efficiency.

SUMMARY OF THE INVENTION

An object of the invention is to provide an absorptive article having wing members jointed reliably.

Another object of the invention is to provide an absorptive article having wing members which can be easily folded downward along edge portions of a crotch portion of an underwear, and a process for manufacturing the absorptive article.

Still another object of the invention is to provide an absorptive article having wing members of excellent air-permeability, and a process for manufacturing the absorptive article.

A further object of the invention is to provide a process for manufacturing an absorptive article which can minimize the trimming loss of the materials to the least while having an excellent production efficiency.

According to the invention, there is provided an absorptive article comprising: a body including a liquid-permeable top sheet, a back sheet and an absorbent layer sandwiched between the top sheet and the back sheet; and wing members disposed on two side portions of the body and extending outwards in the widthwise direction from the body, wherein the wing members are jointed to the two side portions of the body while being sandwiched between the top sheet and the back sheet.

In the invention, the wing members are sandwiched between the top sheet and the back sheet so that they can be reliably jointed to the body while being prevented from coming out when the absorptive article is worn. In the invention, the wing members are made of a material different from those of the top sheet and the back sheet so that they can be given various functions.

Preferably, both the width size of joint regions between the top sheet and the wing members and the width size of joint regions between the back sheet and the wing members are at least 5 mm.

Preferably, at an intermediate region, to which the wing members are attached, of the body, the top sheet has a larger width size than that of the back sheet so that the joint regions between the top sheet and the wing members has a larger width size than that of the joint regions between the back sheet and the wing members.

Preferably, the wing members have a moisture permeability of no less than 10,000 g/m$^2$ according to JIS-Z-0208. In this case, it is preferred that the width size of the joint regions between the top sheet and the wing members is at least 10 mm; that when the area of the joint regions between the top sheet and the wing members is assumed to be 1 (or 100%), the substantial joint area in the joint regions between the top sheet and the wing members by an adhesive is at most 0.2 (or 20%); and that the top sheet and the wing members are partially welded and jointed. More preferably, a plurality of welded and jointed portions are extended in the widthwise direction and provided at intervals in the longitudinal direction such that at least one welded and jointed portion extends from the joint regions between the top sheet and the wing members to regions of only the wing members.

Preferably, the rigidity value of regions, in which the wing members, the top sheet and the back sheet are jointed together, according to the cantilever method is larger by at least 20 mm than that of a joint portion, in which the top sheet and the back sheet are jointed to each other without sandwiching the wing members, according to the cantilever method. In this case, the rigidity value of the wing members according to the cantilever method is preferably 50 to 150 mm in the MD and 30 to 100 mm in the CD.

Preferably, the wing members have an extensibility in the widthwise direction so that the shrinking force of the wing members as a whole for a strain of 10% is at least 5 gf when the wing members are uniformly extended in the widthwise direction all over the area of the longitudinal direction.

Preferably, the wing members have an extensibility in the widthwise direction so that the strain when extended to the limits in the widthwise direction is within a range of 10 to 40%.

Preferably, the wing members have a total-ray transmissivity of at least 20% according to the JIS-K-7105.

According to the invention, there is also provided a process for manufacturing an absorptive article including: a body including a liquid-permeable top sheet, a back sheet and an absorbent layer sandwiched between the top sheet and the back sheet; and wing members disposed on two side portions of the body and extending outwards in the widthwise direction from the body, comprising:

(a) a step of jointing wing member materials to two sides of a back sheet material;

(b) a step of placing an absorbent layer on the back sheet material before or after the step (a);

(c) a step of sandwiching the absorbent layer between a top sheet material and the back sheet material by feeding the top sheet material over the absorbent layer;

(d) a step of jointing the top sheet material and the back sheet material on the outer side of the absorbent layer; and (e) a step of cutting off unnecessary portions of the back sheet material, the top sheet material and the wing member materials, to manufacture an absorptive article in which the body and the wing members are jointed.

According to this manufacture process, the unnecessary portion to be disposed during the manufacture, that is, the so-called "trimming loss" is reduced, and the wing members can be simply attached to the body so that the process is excellent in the productivity.

At the step (a), the wing member materials are preferably jointed to the upper face of the back sheet material, and at the step (c), the wing member materials are preferably sandwiched and jointed between the back sheet material and the top sheet material.

At the step (d), the back sheet material and the top sheet material are preferably jointed by an adhesive.

The process preferably further comprises: between the step (d) and the step (e), the step of welding and jointing the top sheet material and the wing member materials.

DESCRIPTION OF THE PREFERRED EMBODIMENTS

Figure 1:
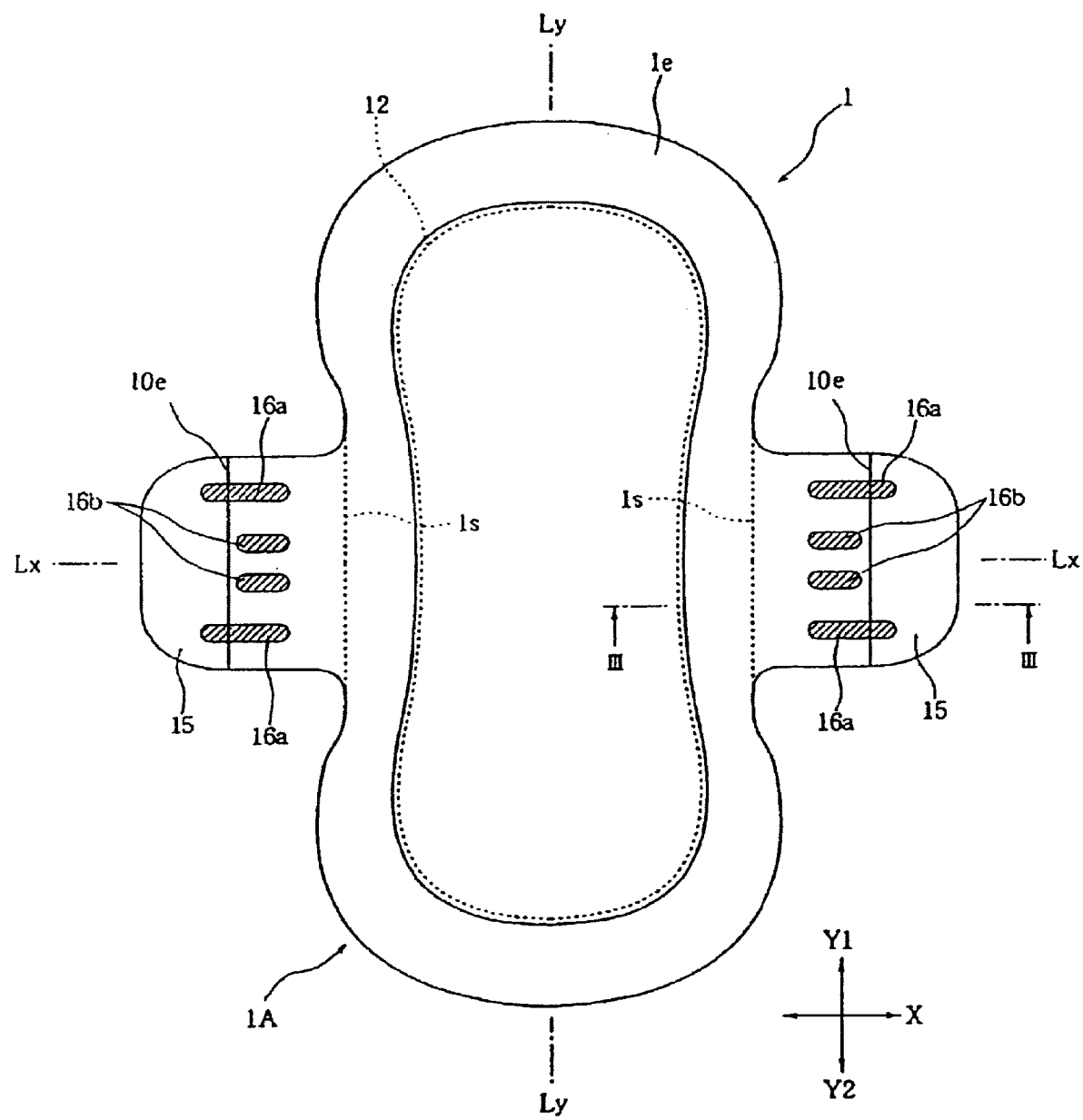
FIG. 1 is a top plan view showing an absorptive article in accordance with one embodiment of the invention and taken from a liquid receiving side.
Figure 2:
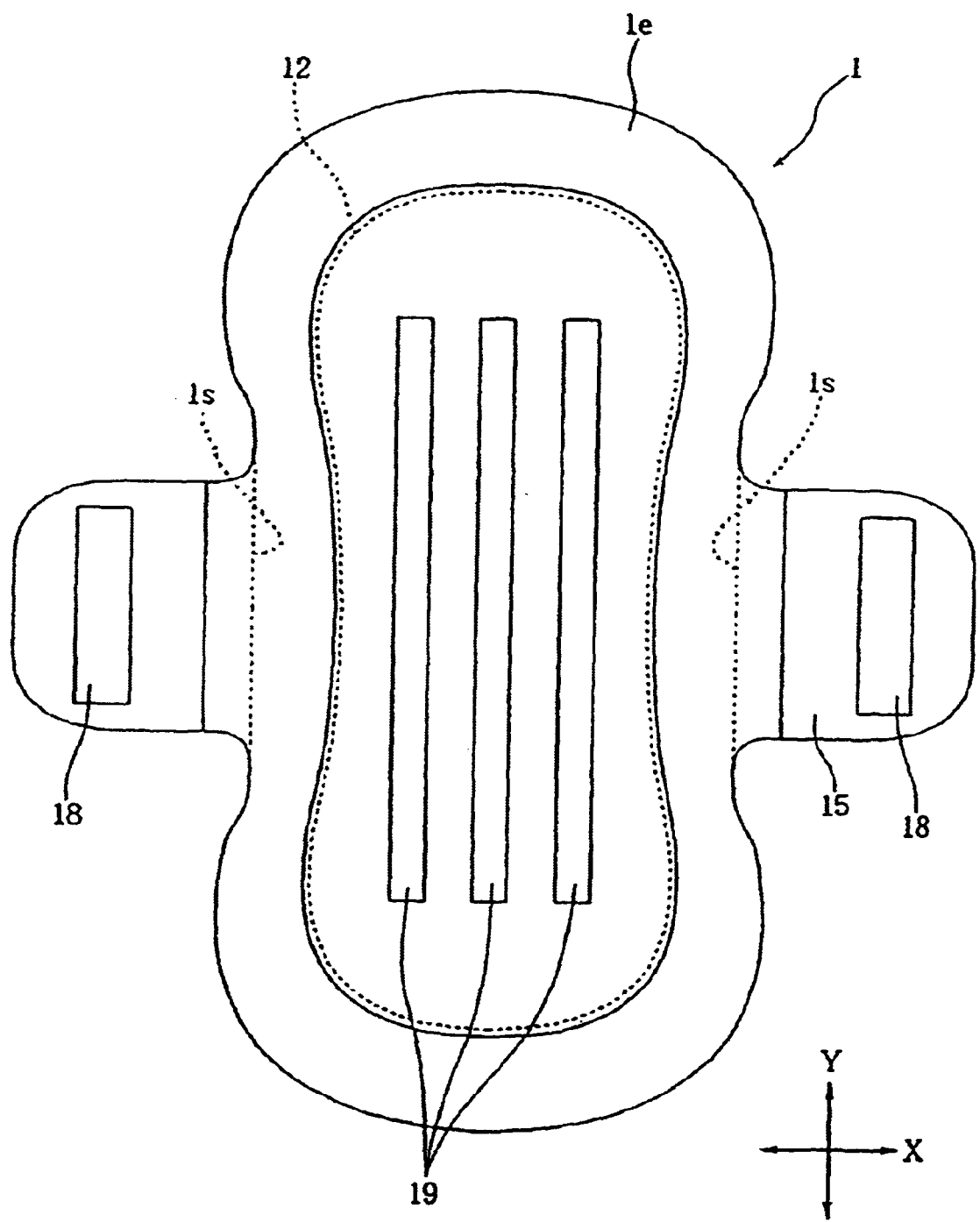
FIG. 2 is a bottom plan view, as taken from the back side, of the absorptive article shown in FIG. 1.
Figure 3:
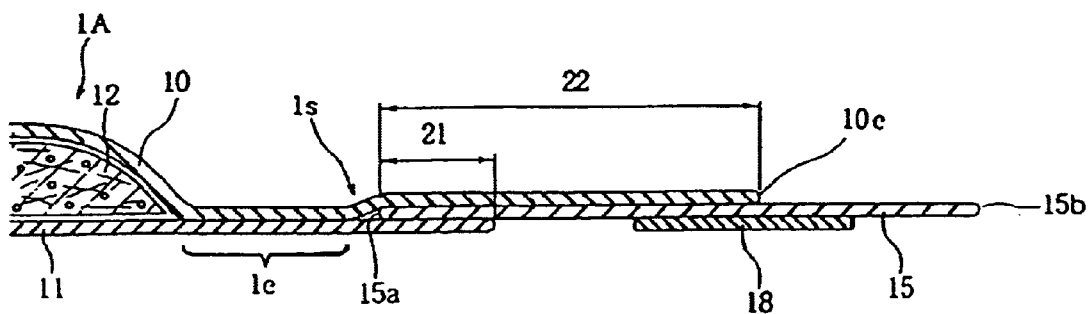
FIG. 3 is a partial section taken along line III—III of FIG. 1.
Figure 4:
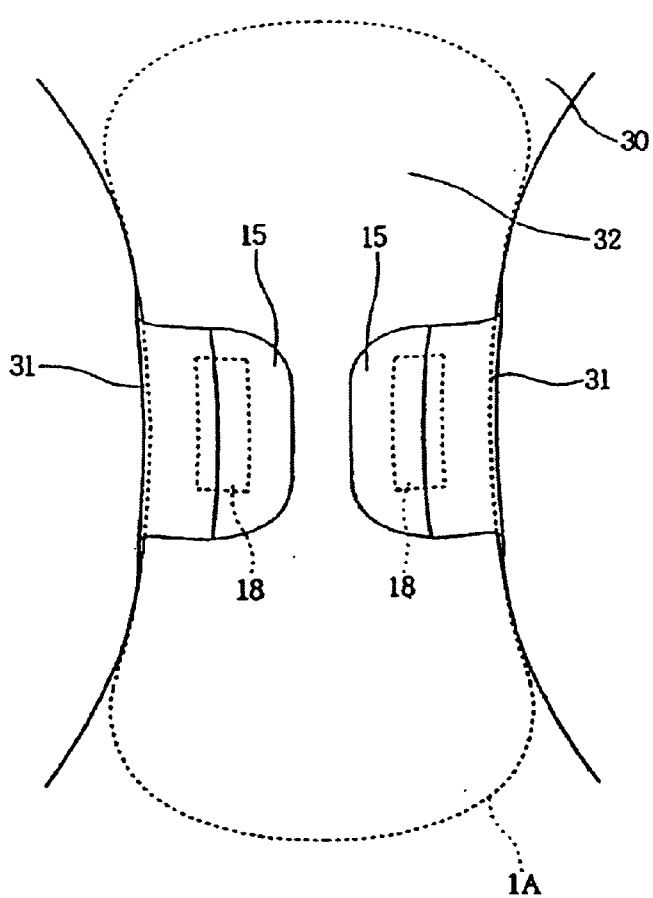
FIG. 4 is a plan view showing the state in which the absorptive article shown in FIG. 1 is mounted on an underwear.

FIG. 1 is a top plan view showing an absorptive article in accordance with one embodiment of the invention and taken from a liquid receiving side; FIG. 2 is a bottom plan view, as taken from the back side, of the absorptive article shown in FIG. 1; FIG. 3 is a partial section taken along line III—III of FIG. 1; and FIG. 4 is a plan view showing the state in which the absorptive article shown in FIG. 1 is mounted on an underwear. Here, a longitudinal direction of the absorptive article is taken in a Y-direction, and a widthwise direction generally perpendicular to the Y-direction is taken in a X-direction.

In the embodiment shown in FIG. 1, the absorptive article of the invention is exemplified by a sanitary napkin 1. This sanitary napkin 1 is made generally symmetric with respect to a center line Ly extending in the Y-direction. The sanitary napkin 1 is constructed, as also seen from the partial sectional view of FIG. 3, to include: a body 1A having a liquid-permeable top sheet 10 directed toward the liquid receiving side, a liquid-impermeable back sheet 11 directed toward the outer side and an absorbent layer 12 sandwiched between the top sheet 10 and the back sheet 11; and wing members 15 disposed on the two longitudinally extending side portions of the body 1A. Moreover, the top sheet 10 and the back sheet 11 are jointed to each other around the absorbent layer 12 by a hot-melt adhesive thereby to form a peripheral joint portion 1e.

As shown in FIG. 2, adhesives 19 are applied to the back of the body 1A of the sanitary napkin 1, and adhesives 18 are applied to the backs of the wing members 15. The sanitary napkin 1 is attached, when worn, to a crotch portion 32 of an underwear 30, as shown in FIG. 4. At this time, the adhesives 19 on the back of the body 1A are retained on the inner face of the crotch portion 32 of the underwear 30. Then, the wing members 15 extending outward of the body 1A in the X-direction are folded together with the extensions of the top sheet 10 along the edge portions 31 of the underwear 30 so that the wing members 15 are retained on the underwear 30 by the adhesives 18. By thus providing the wing members 15, it is possible to prevent the underwear edge portions from being blotted and the sanitary napkin 1 from going out of position.

As shown in FIG. 3, the wing members 15 are sandwiched and jointed at their side portions between the top sheet 10 and the back sheet 11 by an adhesive such as a hot-melt adhesive. The overlapping widths of the joint regions, that is, both the joint width 21 in the X-direction between the back sheet 11 and the wing member 15 and the joint width 22 in the X-direction between the top sheet 10 and the wing member 15 are preferably at least 5 mm or more so that the wing member 15 may not easily leave the body 1A.

In order to enhance the joint strength (or the tearing strength) between the wing member 15 and the body 1A and to fold the wing member 15 easily from the body 1A along the edge portion 31 of the underwear, moreover, the top sheet 10 is preferred to extend longer outward in the X-direction than the back sheet 11. More specifically, in the intermediate region of the body 1A including a center line Lx therein and to be attached with the wing members 15, the size of the top sheet 10 in the X-direction is preferably made so larger than the size of the back sheet 11 in the X-direction that the joint width 22 in the X-direction between the top sheet 10 and the wing member 15 may be larger, as shown in FIG. 3, than the joint width 21 in the X-direction between the back sheet 11 and the wing member 15.

Here, the joint strength (or the tearing strength) between the body 1A and the wing member 15 can also be enhanced by extending the back sheet 11 longer outward in the X-direction than the top sheet 10. Where the back sheet 11 is made liquid-impermeable, however, the moisture permeability of the wings drop if the back sheet 11 is extended outward in the X-direction. For this reason, the joint strength between the body 1A and the wing member 15 is preferably enhanced by making the extending width size of the top sheet 10 in the X-direction larger than that of the back sheet 11 and making the joint width between the top sheet 10 and the wing member 15 so large.

The joint strength (or the tearing strength) between the wing member 15 and the top sheet 10 is preferably 1,000 g(f) or more.

[Measurement 1]

The tearing strength between the wing member 15 and the top sheet 10 was measured in the following manner. A joint assembly, as shown in FIG. 1, of the top sheet 10 and the wing member 15 was manufactured. This assembly is provided with neither the back sheet 11 nor the absorbent layer 12.

One chuck was used to hold the widthwise outer portion of one wing member 15 than the aforementioned joint width 22, i.e., that portion of the wing member 15, which is not jointed to the top sheet 10 but exposed of itself, and the other chuck was used to hold the leading end, as located on the upper side (or the Y1 side), as seen in FIG. 1, of the top sheet 10. When the chuck holding the leading end of the top sheet 10 was pulled in the Y2-direction with the chuck holding the wing member 15 being fixed, the measured value (g) was the load which was applied between the two chucks at the instant when a tear occurred at the joint portion between the top sheet 10 and the wing member 15. In this case, the moving velocity of the other chuck in the Y-direction relative to the one chuck was 100 mm/min.

In the test piece measured, on the other hand, the joint width 22 in the X-direction between the top sheet 10 and the wing member 15 was uniform in the Y-direction. In the joint region of the joint width 22, on the other hand, the hot-melt adhesive was applied intermittently and in a uniform distribution between the top sheet 10 and the wing member 15. If the total area of the joint region of the joint width 22 is set to 1 (or 100%), the applied area (or the substantial joint area) of the hot-melt adhesive in the joint region was 0.5 (or 50%).

Here are enumerated the results of the measurement which were made on the tearing strength for the individual test pieces having different sizes in the joint width 22:

| Joint Width | Tearing strength |
|---|---|
| 5 mm | 500 g |
| 10 mm | 700 g |
| 15 mm | 1,200 g |
| 20 mm | 1,200 g |

From these results, it is preferable that the joint width 22 between the top sheet 10 and the wing member 15 is 15 mm or more. In the joint assembly of the body 1A and the wing member 15, however, the tearing strength can be compensated by the joint between the back sheet 11 and the wing member 15. Therefore, the joint width 22 between the top sheet 10 and the wing member 15 is preferably 10 mm or more. More preferably, the joint width 22 is 15 mm or more.

Next, the wing members 15 are preferably made of an air-permeable sheet so that the underwear may not become highly humid and stuffy in its inside when worn. The moisture permeability of the wing members 15 according to the JIS-Z-0208 is preferably 10,000 $g/m^2 \cdot 24$ h or more.

Moisture Permeability

[JIS Z 0208]

Definition

Moisture permeability is an amount of water vapor which passes through an area of a membranous test piece as a boundary layer when one side of the boundary is kept in relative humidity of 90% and another side is kept dry by a moisture absorbent during 24 hr under 25° C. or 40° C. The measured values for three test pieces are averaged and converted to represent it in g per m square ($g/m^2$).

Measuring Apparatus

Figure 10:
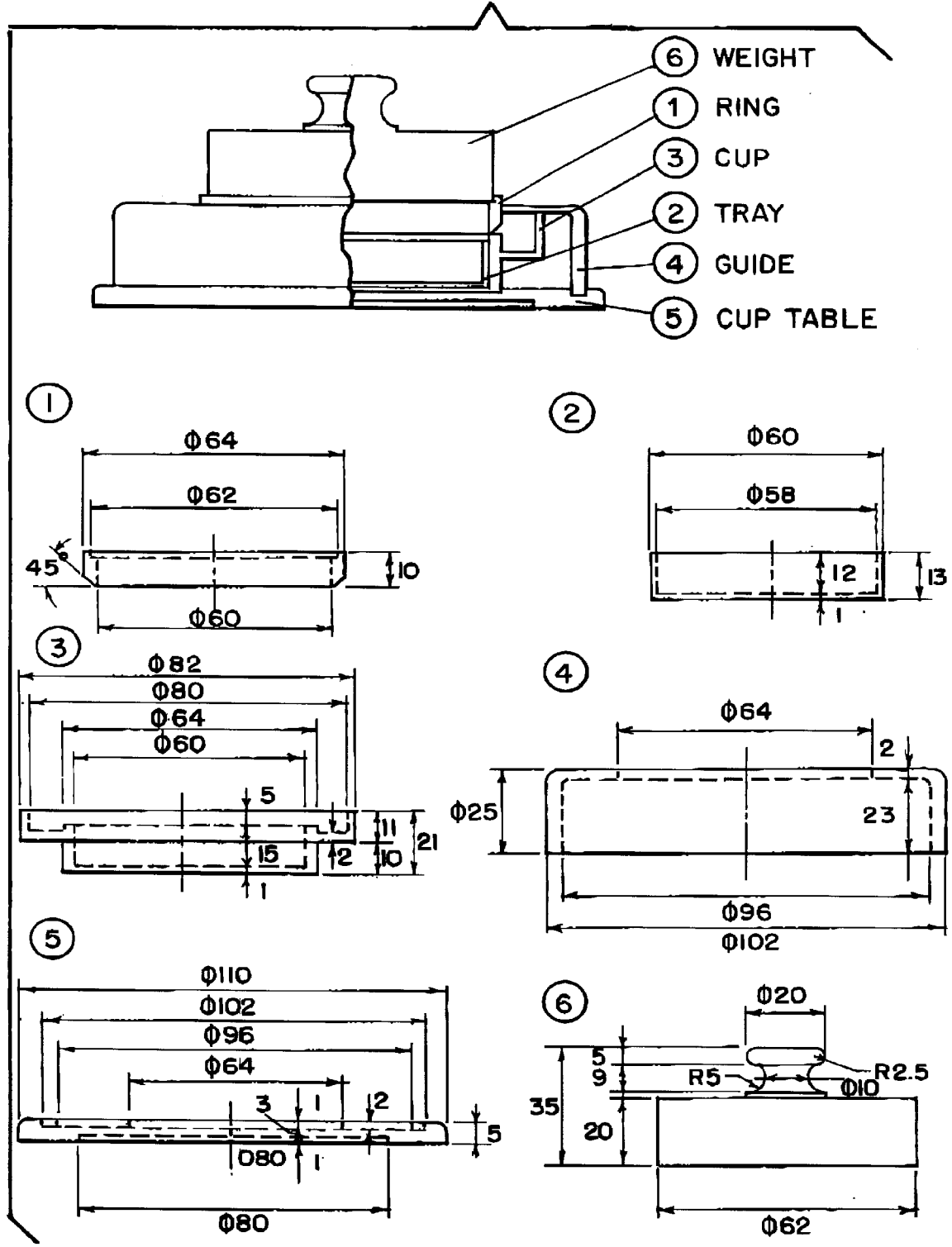
FIG. 10 is a side view of the measuring apparatus of the JIS-Z-0208 Standard)

The measuring apparatus comprising parts designated by numerals 1 to 6 described below is prepared and shown in a side view in FIG. 10. Moisture absorbent made of anhydrous calcium chloride is prepared. A hermetical sealing wax such as 80% paraffin wax with melting point 50–52° C. and 20% polyisobutylene with low polymerization degree is prepared.

| 1. ring | aluminum |
| --- | --- |
| 2. tray | glass |
| 3. cup | anodic oxidized aluminum |
| 4. guide | brass with a central hole |
| 5. cup table | brass with groove on its periphery |
| 6. weight | brass |

Measurement

1. The cup is cleaned and kept at about 30–40° C.
2. The moisture absorbent is placed in the tray to make its surface substantially horizontal in the tray, and both are placed in the cup. The cup is then put on the cup table which is held in a horizontal position.
3. The test piece is put on the cup with concentric configuration such that the surface of the moisture absorbent is arranged about 3 mm lower than the bottom surface of the test piece.
4. The guide is put on a groove of the cup table.
5. The ring is inserted along the hole of the guide in order for the test piece to closely contact the top edge of the cup. The weight is then put on the ring.
6. The guide is pulled up without moving the ring.
7. The sealing wax is poured along the contacting portion for substantially closed packing and cooled.
8. After solidification of the wax, the weight and the cup table are removed.
9. The whole apparatus is stored in a thermostatic oven and stabilized in the test temperature.
10. After storing for over 16 hours, the weight of the whole apparatus is measured at a state of equilibrium.
11. The whole apparatus is again stored in the oven for several hours and measured.
12. The storing and measuring steps are repeated in 24, 48 or 96 hour intervals until two successive results of an increase of the weight per unit time correspond within a margin of error of less than 5% occurs.

On the other hand, the moisture permeability of the top sheet 10 is also preferably 10,000 g/m²·24 h. If the hot-melt adhesive is applied to the whole surface of the joint region of the joint width 22 between the top sheet 10 and the wing member 15, however, the moisture permeability drops in the region where the wing member 15 and the top sheet 10 overlap. Therefore, it is preferable to adjust the adhesive applied area (i.e., the substantial joint area) in the joint region of the joint width 22. However, this adhesive applied area also influences the joint strength (or the tearing strength) between the body 1A and the wing member 15.

[Measurement 2]

Thus, the sample described in the foregoing Measurement 1, i.e., the joint assembly of the top sheet 10 and the wing member 15 was used for measurement of the moisture permeability and its relation to the tearing strength in the joint region of the joint width 22, where the joint width 22 was set at 15 mm (i.e., the lower limit of the preferable range obtained by the Measurement 1) while the adhesive applied area (i.e., the substantial joint area) was varied.

Here, the calculating method of the ratio of the adhesive applied area to the area of the joint region is equal to that described in the Measurement 1. On the other hand, the measurement per se of the tearing strength is also identical to that of the Measurement 1.

The measurement results are as follows (with the moisture permeability being expressed by the unit of g/m²·24 h).

| Adhered Area Ratio | Moisture Permeability | Tearing Strength |
| --- | --- | --- |
| 5% | 95,000 | 300 g |
| 10% | 9,000 | 500 g |
| 20% | 8,000 | 1,000 g |
| 50% | 5,000 | 1,200 g |
| 100% | 0 | 1,200 g |

From these results, it can be said that the moisture permeability takes a preferable value for the adhesive applied area ratio of 20% or less. In such a case, however, since the tearing strength is lowered, it is preferable that the wing member 15 and the top sheet 10 are further jointed by a welding joint (e.g., the heat-sealing, high-frequency melting or ultrasonic welding method) to enhance the joint strength.

In the embodiment shown in FIG. 1, a plurality of heat-sealed portions 16a and 16b extending in the X-direction are provided at intervals in the longitudinal direction so as to enhance the tearing strength without lowering the moisture permeability so much in the range of the joint width 22. At this time, it is preferable that at least one of the heat-sealed portions (e.g., the heat-sealed portions 16a in FIG. 1) extends so far over the range of the joint width 22 as the region where the wing member 15 appears of itself. With these heat-sealed portions 16a and 16b being provided, it is possible to improve the moisture permeability within the region of the joint width 22 and to hold the tearing strength between the top sheet 10 and the wing member 15 at a level of at least 1,200 g or more.

With the heat-sealed portions thus extending to the region where the wing member 15 appears of itself, there is obtained another effect to prevent the two longitudinally extending edge portions of the top sheet 10 (as indicated by 10e) from being peeled from the wing member 15. Where the hot-melt adhesive for jointing the top sheet 10 and the wing member 15 is applied to the area within the joint width 22, more specifically, the edge portions 10e of the top sheet 10 may stick to a manufacturing apparatus to trouble the manufacturing works if the adhesive is applied to the edge portions 10e of the top sheet 10. In an ordinary case, therefore, it is necessary to form a region having a considerable width from the edge portion 10e, to which no adhesive is applied. In this case, the edge portions 10e of the top sheet 10 can be prevented from floating from the wing member 15 if the aforementioned heat-sealed portions 16a and 16b are formed.

On the other hand, it is preferable for the sanitary napkin 1 to be easily folded at its wing portions along the edge portions 31 of the underwear 30. If the rigidity value (as measured by the cantilever method of the JIS L1096) in the regions where the wing members 15, the top sheet 10 and the back sheet 11 are jointed, that is, the regions of the joint width 21 in FIG. 3 is larger by 20 mm or more than that of the joint portion between the top sheet 10 and the back sheet 11, that is, the peripheral joint portion 1e, the wings are easily folded along boundary lines 1s (as located at the root end portions of the wing members 15) between the body 1A and the wing members 15.

In order to bend the wing member 15 more easily along the boundary line 1s, it is preferable to set the rigidity value of the peripheral joint portion 1e (where the top sheet 10 and the back sheet 11 are laminated) to 30 to 80 mm by the cantilever method of the JIS L1096 and the rigidity value of the portion (where the top sheet 10, the back sheet 11 and the wing member 15 are laminated) close to the boundary line 1s on the side of the wing member 15 to 50 to 150 mm.

Cantilever Method
[JIS L 1096]
Method A: 45-Degree Cantilever Method

Figure 11:
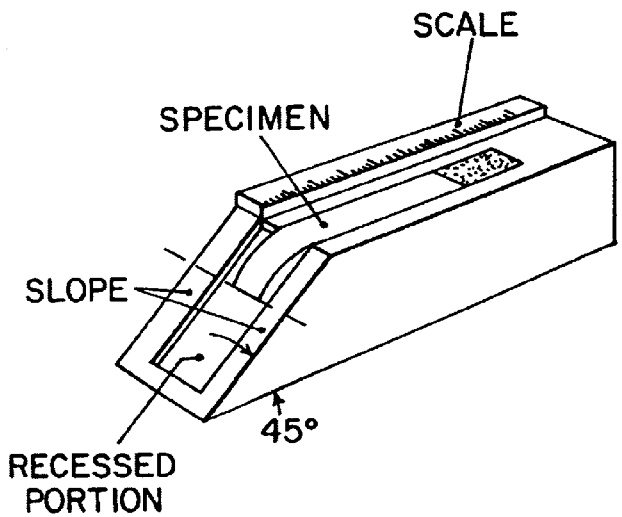
FIG. 11 is a perspective view of the scale used in the JIS-L-1096 Standard)

Five pieces of specimen of 2 cm×about 15 cm are cut out in the machine direction (MD) and the cantilever direction (CD), respectively. The specimen is placed on a horizontal table having a smooth surface and a 45-degree slope at one end thereof while aligning the shorter side of the specimen on a basic line of a scale as shown in FIG. 11. Then, the specimen is then slowly slid toward the slope in an appropriate manner. When one end of the specimen comes into contact at the center thereof with the slope, the position of the other end of the specimen is read by the scale. Bending resistance is expressed by the migration length (mm) of the specimen. The respective five pieces of specimen are tested at both the front surface side and back surface side to obtain average values in MD and CD, respectively (to integral number).

If the rigidity value of the portion close to the boundary line 1s on the side of the wing member 15 is smaller than the aforementioned lower limit (of 50 mm), the wing is hardly folded at the portion of the boundary line 1s but is easily folded at the portion on the widthwise outer side than the boundary line 1s. As a result, there arises a disadvantage that the wing member 15 is folded in the region where the dislocation preventing adhesive 18 is applied, so that the folded portions of the adhesives 18 stick to each other with the result that the wing member 15 is left in the folded state but cannot be returned to the flat shape. Here, if the rigidity value exceeds the aforementioned upper limit (of 150 mm), the wearer of the sanitary napkin may feel a physical disorder.

Here, the rigidity value of the wing member 15 is preferably 50 to 150 mm in MD (Machine Direction) and 30 to 100 mm in CD (Cross Direction). These values reduce the rub on the skin and improve the wearing feel. In this case, moreover, the portion (where the top sheet 10, the back sheet 11 and the wing member 15 are laminated) close to the boundary line 1s on the side of the wing member 15 takes a preferable rigidity value, too.

With the width in the X-direction being 50 mm, on the other hand, the wing member 15 is preferred to extend within a range of 5 to 20 mm in the same direction. Specifically, the wing member 15 is preferred to have such an extensibility that the strain when extended to the widthwise limit may be within a range of 10 to 40%. In the longitudinal direction, however, the wing member 15 is preferred to have no or little extensibility. When the wing members 15 are to be folded downward and retained on the crotch portion 32 of the underwear 30 upon wearing of the sanitary napkin 1, the wing members 15 can be easily retained thereon if they have an extensibility in the X-direction to some extent. In order to allow the wing members 15 to be folded easily on the crotch portion 32, the shrinking force of the entirety of the wing members 15 for the strain of 10% is preferably 5 gf or more when they are extended uniformly in the widthwise direction all over the longitudinal area.

Figure 5:
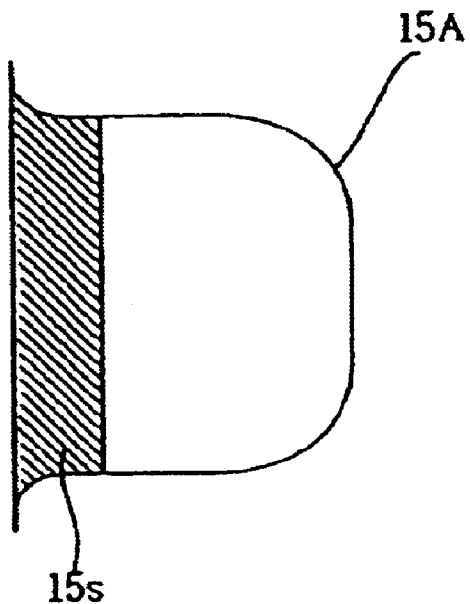
FIG. 5 is a top plan view showing another embodiment of a wing member.
Figure 6:
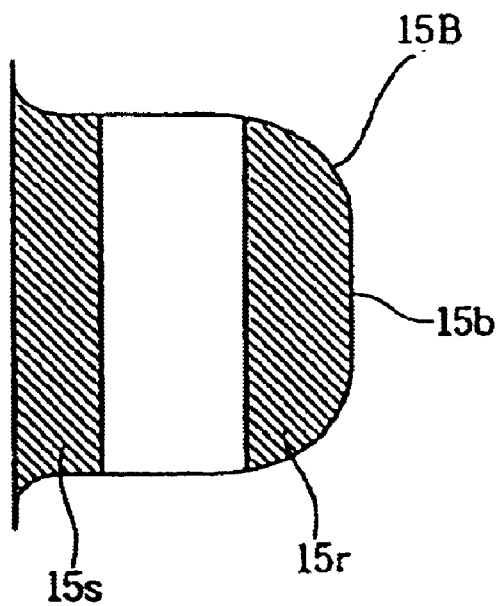
FIG. 6 is a top plan view showing still another embodiment of the wing member.

The wing member 15 may have an extensibility not only in its entirety but also exclusively at a necessary portion. For example, FIG. 5 shows a wing member 15A in which an extensible region 15s is provided only on the side of the boundary line 1s. On the other hand, FIG. 6 shows a wing member 15B in which two extensible regions 15s and 15r are provided on the side of the boundary line is and on the side of an end portion 15b.

Here, in order to make the wing member 15 extensible either entirely or partially (e.g., at the region 15s or at the regions 15s and 15r), the entirety of the wing member 15 can be formed by adhering urethane and spun-bonded nonwoven fabric, or the region 15s or the regions 15s and 15r of the wing member 15 can be formed by adhering urethane and spun-bonded nonwoven fabric partially.

On the other hand, the wing member 15 is preferred to have a total-ray transmissivity of 20% or more according to the JIS-K-7105.

Total Ray Transmissivity
[JIS K 7105]
Measuring Apparatus

Figure 12:
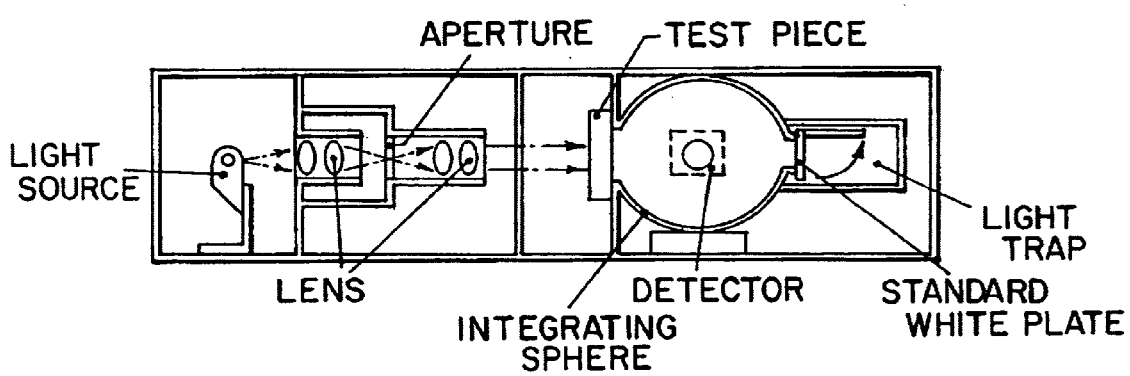
FIG. 12 is a side view of the measuring apparatus of the JIS-L-7105 Standard.
Figure 13:
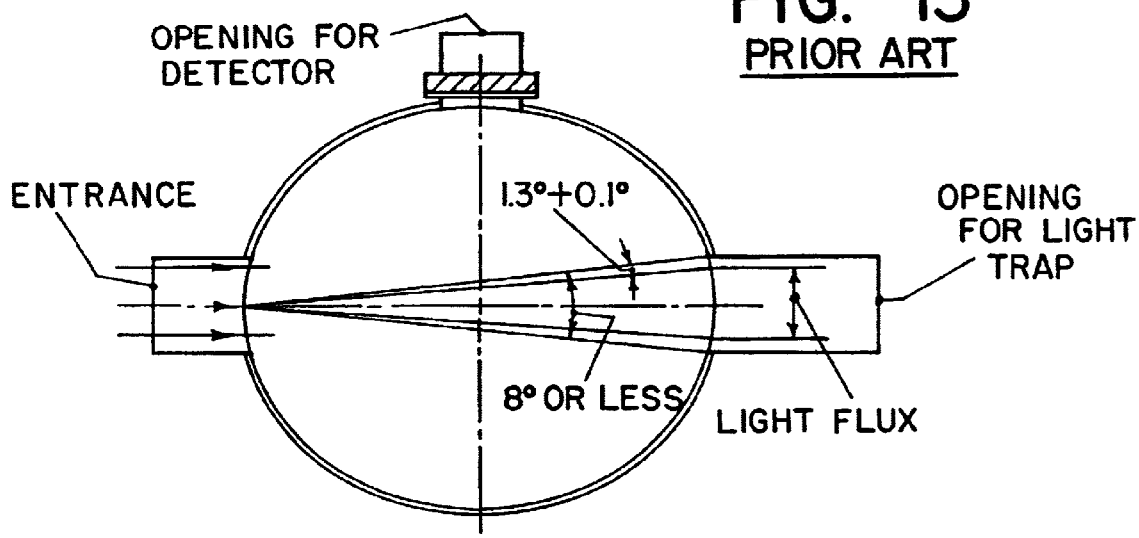
FIG. 13 is a plan view of the measuring apparatus of the JIS-L-7105 Standard.

A measuring apparatus with an integrating sphere is arranged in a configuration as shown in a side view in FIG. 12. A plan view of the integrating sphere is shown in FIG. 13. The total area of the entrance, the opening for detection and the opening for light entrapment must be less than 4% of total inner sphere. A standard white plate is prepared with a surface of reflective material such as magnesium oxide, barium sulfate and aluminum oxide. The inner surface of the integrating sphere is coated with the same material as the standard reflection plate. A light flux is arranged by the artificial sunlight to be parallel in order not to include any ray which is shifted over 3 degrees from the axis of the flux. The axis of flux is arranged to match a line extending between the centers of the entrance and the opening for the light trap.

Measurement

1. Three pieces of the wing member with a size which can cover the entrance are prepared.
2. The standard white plate is set and the flux is introduced without the test piece and the value of detector is read as T1.
3. Then the test piece is set and the value for the material is read as T2.
4. The measurement is repeated for three test pieces respectively.
5. The transmissivity T is obtained as the average of T2/T1 (percentage). The light trap is not used for this purpose.

The wing members 15 are fixed on the outer side of the underwear 30 at the crotch portion of the underwear 30, as shown in FIG. 4. With the high ray transmissivity of the wing members 15, therefore, the color of the underwear 30 is seen through the wing members 15 so that the worn sanitary napkin is hardly recognized. Where the wing members 15 are made of a nonwoven fabric, for example, this nonwoven fabric is preferably made of an undulled sheet containing no plasticizer such as titanium. Alternatively, for example, the wing members 15 may be made of a transparent film.

The wing members 15 can be made of a nonwoven fabric or a film, for example. Preferred is a thermal bonded nonwoven fabric of polypropylene. More preferred is a lamination of a spun-bonded nonwoven fabric, a melt blown nonwoven fabric and a spun-bonded nonwoven fabric.

The top sheet 10 can be made of hydrophobic fibers subjected to a hydrophilic treatment, hydrophilic fibers or the like, such as point-bonded, air-through, spun-bonded or spun-lace nonwoven fabric. Alternatively, the top sheet 10 may be formed by laying a cushion layer of bulky nonwoven fabric over the above-specified nonwoven fabric.

The back sheet 11 is made liquid-impermeable but air-permeable of a resin sheet of polyolefins, for example. Alternatively, the back sheet 11 may be made of a nonwoven fabric and a waterproof film sandwiched between the nonwoven fabric and the absorbent layer 12.

The absorbent layer 12 is made of an absorbent material, as exemplified by: a fibrous web of hydrophilic fibers such as those of rayon, cotton or the like; pulverized pulp; or a mixture of pulverized pulp and a highly water-absorbent polymer. Alternatively, the absorbent material is prepared by enveloping the pulverized pulp or the mixture of the pulverized pulp and the highly water-absorbent polymer with an absorbent sheet such as tissues.

Next, a process for manufacturing the sanitary napkin 1 shown in FIG. 1 will be described with reference to FIGS. 7 to 9.

Figure 7:
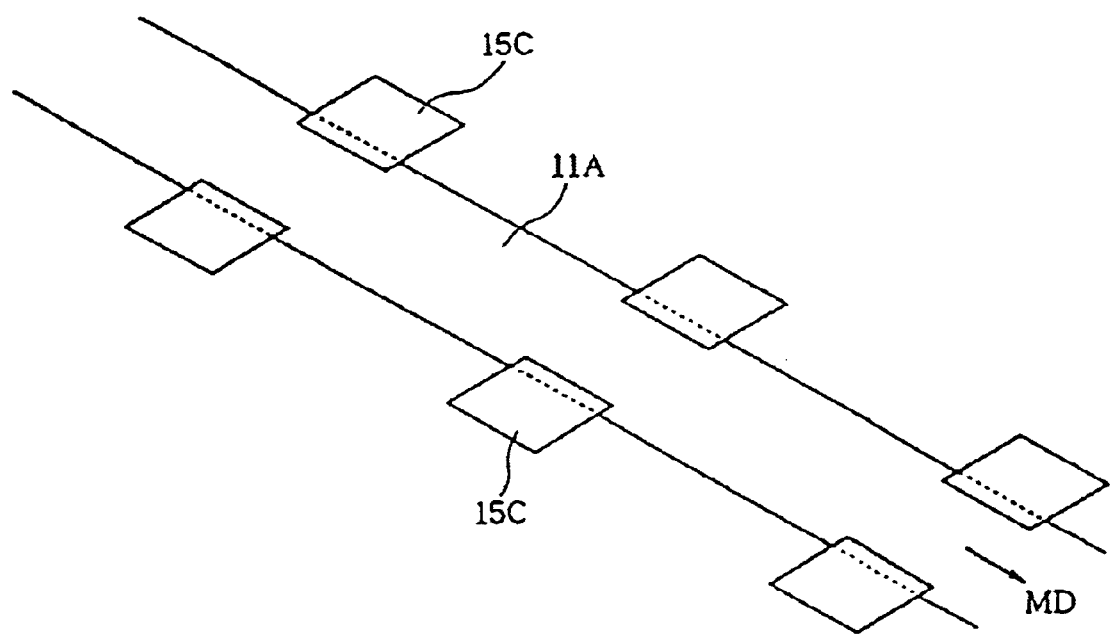
FIG. 7 is a process chart for explaining the state in which a back sheet material and a wind member material are fed.

First of all, wing member materials 15C of a rectangular shape are jointed to the two side portions of a band-shaped back sheet material 11A being continuously fed, as shown in FIG. 7. These wing member materials 15C are cut away from a band-shaped material and are fed at intervals in the MD so that they are bonded to the back sheet material 11A by a hot-melt adhesive.

Figure 8:
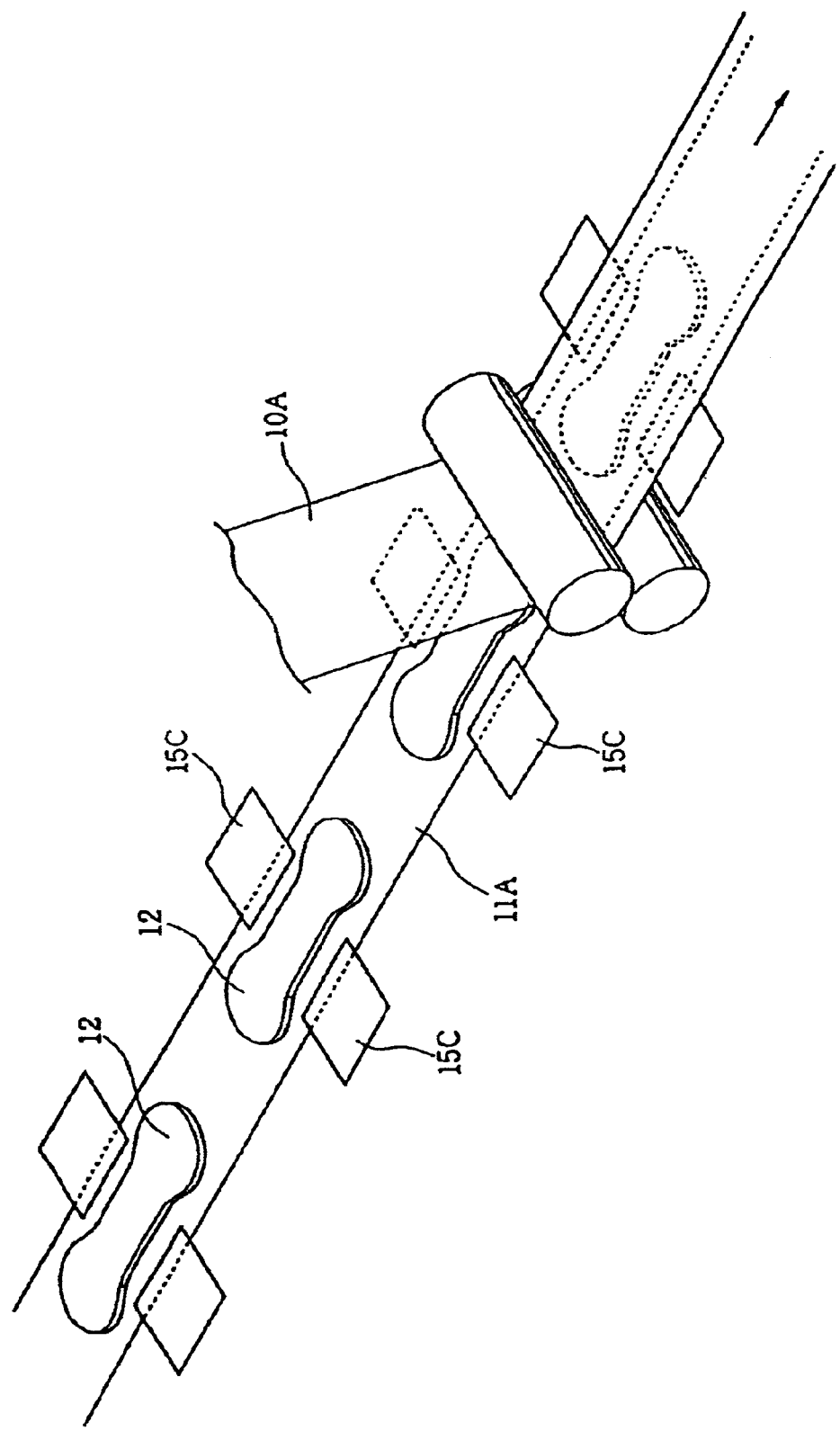
FIG. 8 is a process chart for explaining the state in which an absorbent layer and a top sheet material are fed.

Next, as shown in FIG. 8, the absorbent layers 12 are intermittently fed, each of which is placed on the back sheet material 11A and between the wing member materials 15C and 15C. At this time, the back sheet material 11A and the absorbent layer 12 are jointed by a hot-melt adhesive or the like. Alternatively, the wing member materials 15C may be adhered and jointed to the back sheet material 11A after the absorbent layer 12 was fed onto the back sheet material 11A.

After this, a top sheet material 10A is continuously fed so that the absorbent layer 12 is sandwiched between the back sheet material 11A and the top sheet material 10A. At this time, the top sheet material 10A and the back sheet material 11A are adhered to each other at the periphery of the absorbent layer 12 by a hot-melt adhesive which has been applied in advance to the back sheet material 11A. Also, the top sheet material 10A and the wing member materials 15C are adhered to each other by a hot-melt adhesive.

Figure 9:
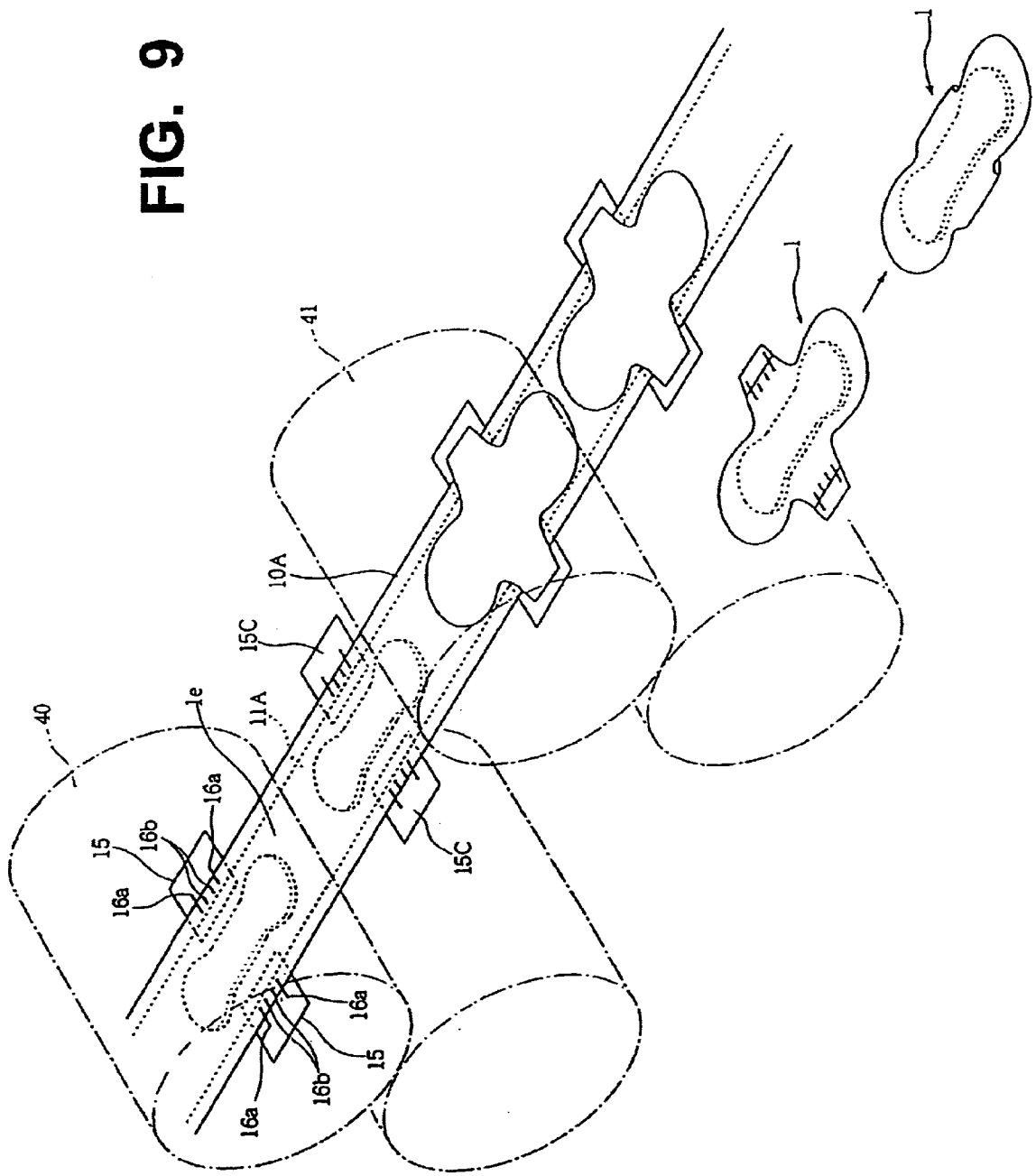
FIG. 9 is a final process chart for obtaining a sanitary napkin.

As shown in FIG. 9, moreover, the peripheral portion of the absorbent layer 12 is heat-sealed by a first roll 40 so that the top sheet material 10A and the back sheet material 11A are jointed at the periphery of the absorbent layer 12 to form the peripheral joint portion 1e. Simultaneously with this, the heat-sealed portions 16a and 16b are formed at the joint portions between the top sheet material 10A and the wing member materials 15C.

By a second roll 41, thereafter, the unnecessary portions are removed (by a trimming or trim-cutting method). The sanitary napkin 1 thus cut is folded at its wing members 15 toward the back sheet or top sheet side. At this time, the folding step can be simply advanced if the wing members 15 are made easily foldable along the boundary lines 1s, as described hereinbefore. Although not shown, moreover, the sanitary napkin 1 is folded in three or four and are individually packaged.

By the process thus far described, the wing members can be attached simply and reliably to the body 1A. According to this manufacture method of the invention, on the other hand, the portions to be disposed are less (with little trimming loss) than those of the case of the prior art in which the top sheet material is extended outwards of the widthwise direction to form the wings, that is, in which the top sheet material is extended to have a width containing the wings and the unnecessary portions are cut off.

Here, the absorptive article having the wing members of the invention should not be limited to the sanitary napkin thus far described but can be applied to pantie liners, urine pads or the like. Moreover, the entire shape of the absorptive article is suitably modified according to its using purpose. On the other hand, the absorptive article can be provided on its two side portions with transverse leakage preventing barrier cuffs (or side gathers), as called so.

In the absorptive article of the invention, as has been described hereinbefore, the wing members will not easily come out of the body. Moreover, the wing members can be reliably jointed to the body while retaining the moisture permeability and the air permeability. By adjusting the rigidities of the body and the wing members, moreover, the wing members can be easily folded at the side portions of the body. This easy folding makes it easy to wear the absorptive article and to fold the same while being manufactured.

According to the process for manufacturing the absorptive article of the invention, on the other hand, the portions to be disposed during the manufacture process can be reduced, and the absorptive article can be easily manufactured, so that the productivity can be enhanced.

Here, "comprises/comprising" when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. An absorptive article comprising:
   a body including a liquid-permeable top sheet, a back sheet and an absorbent layer sandwiched between said top sheet and said back sheet; and
   wing members extending outwards in a latitudinal direction from said body,
   wherein said top sheet and said back sheet extend beyond the periphery of said absorbent layer to have a peripheral joint portion in which said top sheet and said back sheet are adjoined together without having the wing members therebetween, and further extend outwards in the latitudinal direction such that protruding portions are formed, and
   wherein only a portion of each wing member is joined to a corresponding one of two protruding portions of said body while being sandwiched between said top sheet and said back sheet so that a remaining portion of each wing member extends outwards without overlapping the top sheet and the back sheet.

2. The absorptive article as set forth in claim 1, wherein a latitudinal dimension of joint regions between said top sheet and said wing members and a latitudinal dimension of joint regions between said back sheet and said wing members are at least 5 mm.

3. The absorptive article as set forth in claim 2, wherein at an intermediate region of said body to which said wing members are attached, said top sheet has a larger latitudinal dimension than that of said back sheet so that the joint regions between said top sheet and said wing members have a larger latitudinal dimension than that of the joint regions between said back sheet and said wing members.

4. The absorptive article as set forth in claim 3, wherein said wing members have a moisture permeability of no less than 10,000 g/m$^2$ in accordance with JIS-Z-0208.

5. The absorptive article as set forth in claim 4, wherein the latitudinal dimension of said joint regions between said top sheet and said wing members is at least 10 mm,
   wherein when an area of said joint regions between said top sheet and said wing members is substantially 1 or 100%, a substantial joint area in said joint regions between said top sheet and said wing members by an adhesive is at most 0.2 or 20%, and wherein said top sheet and said wing members are partially welded and jointed.

6. The absorptive article as set forth in claim 5, wherein a plurality of welded and jointed portions extend in the latitudinal direction and are provided at intervals in the longitudinal direction such that at least one welded and jointed portion extends from said joint regions between said top sheet and said wing members to regions of only said wing members.

7. The absorptive article as set forth in claim 1, wherein a rigidity value of regions, in which said wing members, said top sheet and said back sheet are jointed together, in accordance with a cantilever method JIS L 1096 is larger by at least 20 mm than that of a joint portion, in which said top sheet and said back sheet are adjoined to each other without sandwiching said wing members, in accordance with the cantilever method.

8. The absorptive article as set forth in claim 7, wherein the rigidity value of said wing members in accordance with the cantilever method is 50 to 150 mm in an MD and 30 to 100 mm in a CD.

9. The absorptive article as set forth in claim 1, wherein said wing members have an extensibility in said latitudinal direction so that a shrinking force of said wing members as a whole for a strain of 10% is at least 5 gf when said wing members are uniformly extended in the latitudinal direction over an entire area in the longitudinal direction.

10. The absorptive article as set forth in claim 1, wherein said wing members have an extensibility in said latitudinal direction so that a strain when extended to the limits in said latitudinal direction is within a range of 10 to 40%.

11. The absorptive article as set forth in claim 1, wherein said wing members have a total-ray transmissivity of at least 20% in accordance with JIS-K-7105.

12. An absorptive article comprising:
  a body including a liquid-permeable top sheet, a back sheet and an absorbent layer sandwiched between said top sheet and said back sheet; and
  wing members having a moisture permeability of no less than 10,000 g/m² in accordance with JIS-Z-0208 extending outwards in a latitudinal direction from said body;
  wherein said top sheet and said back sheet extend beyond the periphery of said absorbent layer to have a peripheral joint portion in which said top sheet and said back sheet are adjoined together without having the wing members therebetween, and further extend outwards in the latitudinal direction such that protruding portions are formed,
  each wing member is jointed to a corresponding one of two protruding portions of said body while being sandwiched between said top sheet and said back sheet,
  a latitudinal dimension of joint regions between said top sheet and said wing members and a latitudinal dimension of joint regions between said back sheet and said wing members are at least 5 mm,
  at an intermediate region of said body to which said wing members are attached, said top sheet has a larger latitudinal dimension than that of said back sheet so that the joint regions between said top sheet and said wing members have a larger latitudinal dimension than that of the joint regions between said back sheet and said wing members,
  the latitudinal dimension of said joint regions between said top sheet and said wing members is at least 10 mm,
  when an area of said joint regions between said top sheet and said wing members is substantially 1 or 100%, a substantial joint area in said joint regions between said top sheet and said wing members by an adhesive is at most 0.2 or 20%, and wherein
  said top sheet and said wing members are partially welded and jointed.

13. An absorptive article comprising:
  a body including a liquid-permeable top sheet, a back sheet and an absorbent layer sandwiched between said top sheet and said back sheet; and
  wing members having a total-ray transmissivity of at least 20% in accordance with JIS-K-7105 extending outwards in a latitudinal direction from said body,
  wherein said top sheet and said back sheet extend beyond the periphery of said absorbent layer to have a peripheral joint portion in which said top sheet and said back sheet are adjoined together without having the wing members therebetween, and further extend outwards in the latitudinal direction such that protruding portions are formed, and wherein
    each wing member is jointed to a corresponding one of two protruding portions of said body while being sandwiched between said top sheet and said back sheet.

* * * * *